(12) United States Patent
Romagnoli

(10) Patent No.: US 11,690,764 B2
(45) Date of Patent: Jul. 4, 2023

(54) HYGIENE STICK FOR PERSONAL CARE

(71) Applicant: TECHPOL S.r.l., Morro d'Alba (IT)

(72) Inventor: Maurizio Romagnoli, Morro d'Alba (IT)

( * ) Notice: Subject to any disclaimer, the term of this patent is extended or adjusted under 35 U.S.C. 154(b) by 549 days.

(21) Appl. No.: 16/470,219

(22) PCT Filed: Dec. 19, 2017

(86) PCT No.: PCT/IT2017/000287
§ 371 (c)(1),
(2) Date: Jun. 16, 2019

(87) PCT Pub. No.: WO2018/116330
PCT Pub. Date: Jun. 28, 2018

(65) Prior Publication Data
US 2019/0321228 A1    Oct. 24, 2019

(30) Foreign Application Priority Data
Dec. 20, 2016   (IT) ..................... 102016000128780

(51) Int. Cl.
*A61F 11/00*   (2006.01)

(52) U.S. Cl.
CPC .................. *A61F 11/006* (2013.01)

(58) Field of Classification Search
CPC .. A61M 3/0279; A61M 1/008; A61M 1/0031; A61F 11/00; A61F 11/006; A61F 11/06; A61F 11/08; A61F 13/38; A61B 17/24; A61B 2017/246
See application file for complete search history.

(56) References Cited

U.S. PATENT DOCUMENTS

| | | | | |
|---|---|---|---|---|
| 4,168,697 A | * | 9/1979 | Cantekin | A61F 11/002 128/867 |
| 4,411,265 A | * | 10/1983 | Eichenlaub | A61M 3/0204 606/161 |
| 5,107,861 A | * | 4/1992 | Narboni | A61F 13/38 128/846 |
| 5,176,654 A | * | 1/1993 | Schreiber | A61F 11/00 604/181 |
| 5,421,818 A | * | 6/1995 | Arenberg | A61M 31/00 604/20 |
| 5,632,756 A | * | 5/1997 | Kruglick | A61F 11/006 606/162 |
| 5,665,094 A | * | 9/1997 | Goldenberg | A61F 11/004 604/212 |
| 5,674,196 A | * | 10/1997 | Donaldson | A61M 3/0262 604/174 |

(Continued)

FOREIGN PATENT DOCUMENTS

| | | |
|---|---|---|
| FR | 2249640 A1 | 5/1975 |
| FR | 2761259 A1 | 10/1998 |
| WO | 2015/122651 A1 | 8/2015 |

*Primary Examiner* — Majid Jamialahmadi
(74) *Attorney, Agent, or Firm* — Patshegen IP; Moshe Pinchas

(57) ABSTRACT

A hygiene stick (1), for personal care, in particular for ear hygiene, comprises a rod (2) for picking up and handling with the fingers and at least one head (3) supported by said rod (2). The head (3) is made of elastic material and is supported cantilever-style by said rod (2) projecting from the rod along an axial line (5).

10 Claims, 1 Drawing Sheet

(56) References Cited

U.S. PATENT DOCUMENTS

| | | | | |
|---|---|---|---|---|
| 5,919,130 | A * | 7/1999 | Monroe | A61B 1/227 600/129 |
| 5,954,682 | A * | 9/1999 | Petrus | A61F 11/00 128/898 |
| 6,358,231 | B1 * | 3/2002 | Schindler | A61F 11/00 604/1 |
| 6,725,568 | B2 * | 4/2004 | Gronka | A61F 11/006 34/104 |
| 7,951,106 | B1 | 5/2011 | Perez et al. | |
| 8,052,693 | B2 * | 11/2011 | Shahoian | A61B 5/0077 606/109 |
| 2002/0069883 | A1 * | 6/2002 | Hirchenbain | A61F 11/08 128/867 |
| 2006/0167469 | A1 * | 7/2006 | Arden | A61M 1/0043 606/109 |
| 2006/0253087 | A1 * | 11/2006 | Vlodaver | A61M 31/00 604/275 |
| 2007/0167918 | A1 * | 7/2007 | Reed | A61M 1/0064 604/187 |
| 2008/0051804 | A1 * | 2/2008 | Cottier | A61F 11/002 606/109 |
| 2008/0142385 | A1 * | 6/2008 | Stein | A61F 13/38 206/362 |
| 2008/0154343 | A1 * | 6/2008 | Li | A61B 18/22 607/89 |
| 2008/0183125 | A1 * | 7/2008 | Issa | A61F 11/006 604/26 |
| 2008/0262508 | A1 * | 10/2008 | Clifford | A61M 31/00 606/109 |
| 2008/0262509 | A1 * | 10/2008 | Clifford | A61N 1/306 606/109 |
| 2009/0197956 | A1 * | 8/2009 | Disbrow | A61K 9/0095 514/561 |
| 2010/0274188 | A1 * | 10/2010 | Chang | A61B 1/227 604/96.01 |
| 2011/0066172 | A1 * | 3/2011 | Silverstein | A61F 13/38 606/162 |
| 2011/0301572 | A1 * | 12/2011 | Vlodaver | A61M 31/00 604/514 |
| 2012/0059224 | A1 * | 3/2012 | Wellen | A61B 1/227 600/200 |
| 2012/0071824 | A1 * | 3/2012 | Chang | A61B 17/32002 604/96.01 |
| 2012/0283616 | A1 * | 11/2012 | Edme | A61F 13/38 604/1 |

* cited by examiner

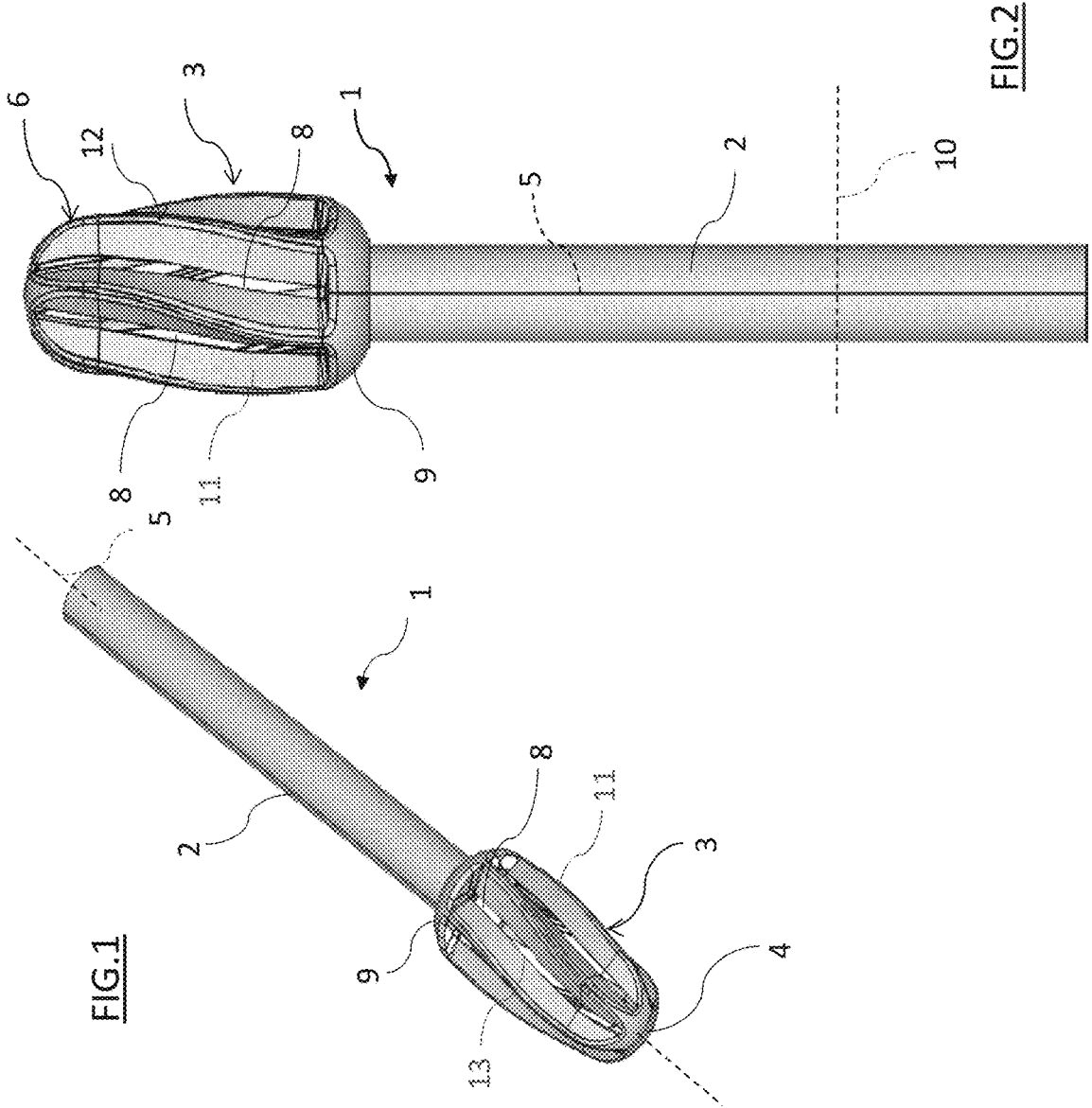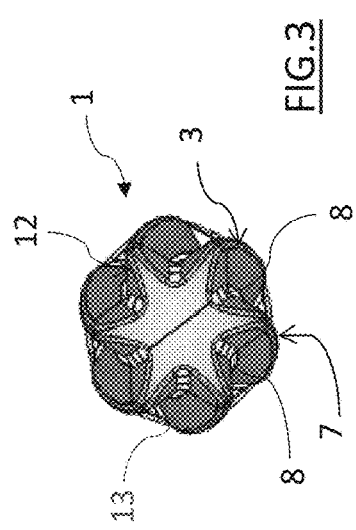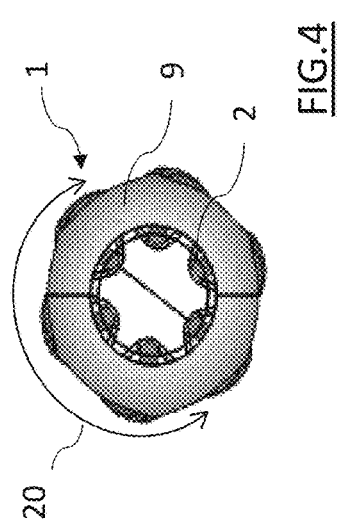

HYGIENE STICK FOR PERSONAL CARE

TECHNICAL FIELD

This invention relates to a hygiene stick for personal care, in particular for ear hygiene.

BACKGROUND ART

Disposable sticks are well known for ear hygiene. They usually comprise a short, thin rod made of semi-rigid material, which at one or both ends is covered with a cotton wad that is tightly wound and glued to the rod. The rod has a central part or an end stretch that can be gripped by the user for picking up the hygiene stick and handling it with the fingers during use.

Hygiene sticks of the type referred to above, although often and widely used daily by many people, have several potential and major disadvantages that could be brought to light extremely easily by inappropriate use of them. In fact, if the stick is inserted too far into the ear canal, it may hurt or damage the eardrum, which in the worst case scenario could even result in permanent hearing damage.

The pushing action of the stick on the eardrum, whether directly or transmitted to it through the interposed ear anatomical humours, may in fact damage the eardrum due to the intrinsic rigidity of the rod, attributable on one hand to the material of which the rod is made and, on the other hand, to the end-on movement of the stick used in the ear canal.

With regard to that, it should also be noticed that the cotton, although in itself very soft, is not able to provide any practical attenuation of that disadvantage, since running through its entire length there is a corresponding, equally long, end stretch of the rod that constitutes an inner stiffening core and support around which the cotton fibres are tightly wound.

However, a possible further disadvantage, attributable to the cotton wad is the fact that were the latter not to form a perfectly monolithic assembly with the rod, it would be susceptible to potential detachment and release inside the ear canal, resulting in considerable inconvenience for the user, including the need to go to medical staff in order to have it removed without complications.

To overcome such disadvantages, document FR 2249640 describes a hygiene stick equipped with a pad having the shape of a solid of revolution and constituted of the cover of a plurality of flexible thin plates extending in a helical shape. The thin plates are supported cantilever-style by a cylindrical sleeve, inside the pad, which is worn on an end stretch of the rod of the stick that is made of rigid material.

In contrast, document US2008/0142385 refers to a device for ear wax removal, that comprises a shaft, at one end of which there is a receiving unit on which a small head is mounted. The latter comprises a plurality of grooves that surround it with an angle optimised for cleaning the ear canal when the shaft is rotated.

The receiving unit has a rigid structure formed by a hemisphere type end that is positioned on a pair of supporting legs which are supported by a plate.

The small head contains the receiving unit that longitudinally penetrates its inner cavity, being covered by it and that hooks the small head to the rod.

The small head is equipped with a tickler located on its outer surface, which when the stick is used is facing the eardrum.

Document U.S. Pat. No. 7,951,106 describes a solution with a bulbous end consisting of a spherical, hollow head, in communication with a tube that is also hollow. The hollow head is monolithic with a sleeve that is fitted, with overlap, on an end stretch of the tube.

In contrast, document US2012/0283616 describes sticks having hollow heads at one of the ends. The hollow heads are integrated in a single body with rods for picking up and handling the stick with one's fingers.

DISCLOSURE OF THE INVENTION

According to the invention, that result is achieved by means of a hygiene stick whose technical features are clearly described in the claims herein.

BRIEF DESCRIPTION OF THE DRAWINGS

The advantages of the invention are more apparent in the detailed description which follows, with reference to the accompanying drawings which illustrate example, non-limiting embodiments of the invention, in which:

FIG. 1 is a three-dimensional perspective view showing the invention as a whole;

FIG. 2 is a perspective view of the invention;

FIGS. 3 and 4 are front and rear views of the invention viewed axially.

DETAILED DESCRIPTION OF PREFERRED EMBODIMENT OF THE INVENTION

With reference to the figures of the accompanying drawings, the reference character 1 denotes in its entirety a hygiene stick, for personal care, in particular for ear hygiene.

The stick 1 basically comprises a rod 2 for picking up and handling with the fingers; and one or more heads 3, supported by said rod 2, which are made of elastic material and are supported cantilever-style by the rod 2, projecting from the rod along an axial line 5, from one or both of its opposite ends.

The hygiene stick 1 is preferably made of elastomeric materials which at said one or each head 3 and said rod 2 have different hardness and rigidity.

The head 3 of the stick 1 preferably has the shape of a hollow geometric solid, with axial symmetry, adapted for making the stick 1 suitable for rotating about the axial line 5 of the rod 2, as indicated by the arrow 20.

As is clearly shown in the figures of the accompanying drawings, the head 3 of the stick 1 has a tapered shape, converging towards its free end 4 that is distal from the rod 2.

That tapered shaped is preferably essentially conical, in conformity with the geometry and the anatomical dimensions of the ear canal.

The head 3 is equipped with a rounded cap 6, supported at its free end 4. It is also, preferably, equipped with a lateral wall 7 through which a set of through slits 8 pass. The slits are substantially elongate longitudinally relative to the rod 2.

Interposed between the head 3 and the rod 2, the stick 1 has a supporting base 9 for the head 3, which is preferably a cap, fixed to the rod 2, and widened along a line 10 transversal to the rod.

As a result of the elasticity of the material used to make it, the head 3—should it be in a condition to apply a thrust that is too strong on the eardrum, or on the interposed anatomical humours which could in turn convey said thrust to the eardrum—yields, elastically deforming, thereby damping said thrust without causing appreciable pain or damage to the eardrum.

That potentially damaging effect is also further inhibited by the fact that the head 3 is rounded so as to provide a large contact surface area, and therefore low localised pressure that, avoiding concentration of the thrust on a limited area of the eardrum, further attenuates the risk of possible damage by perforation. It is also clear that a further safety feature against the risk of damage by inserting the stick 3 too far towards the eardrum is also provided by the supporting base 9 of the head 3, which due to its shape—once the stick 1 maximum penetration limit has been reached in the ear canal—laterally makes contact with and is stopped against the conical walls of the ear canal, thereby preventing the stick 1 from advancing any further towards the eardrum.

An elastic material with properties suitable for providing the damping effect may be an elastomer, selected from the families of rubbers, or the families of thermoplastics, which, for example, have a hardness not greater than 15/20 degrees Shore.

It should be noticed that the through slits 8 may also contribute to definition of the overall elastic properties of the head 3, particularly along the axial line 5 of the rod 2. In fact, the slits 8 are able to influence—due to their geometrical shape—the elastic deformability of the head 3. In other words, by suitably combining the elastic properties of the material used to make the head 3 with the length and number of slits 8, it is possible to modulate the transversal resistance of the head 3 and, therefore, to affect the overall shock absorption capacity relative to the accidental thrust towards the eardrum, in such a way as to minimise the risk of causing harm to the stick 1 user.

The head 3 also preferably has an outer lateral surface 11 having a corrugated design.

Preferably, the outer lateral surface 11 of the head 3 is provided with projections 12 extending mainly longitudinally relative to said head 3. The projections 12 are alternated in an orderly way with channels 13 that are longitudinal relative to the head.

The projections 12 of the head 3 have a cross-section basically with three-sided geometry and substantially extend along the entire length of the head 3.

As is clear in the figures, the projections 12 have a helical shape wrapped around the axial line 5 of the rod 2.

Moreover, the slits 8 and the projections 12 are alternated in an orderly way along a circular outline of the head 3.

The slits 8 allow a liquid or gelatinous substance that may be contained in the head 3 to be able to reach the inside of the ear canal through said slits 8.

If the rod 2 is also tubular, communicating with said hollow head 3, the rod 2 may usefully act as a cartridge for containing liquid or gelatinous substances to be inserted in the ear canal for the most diverse reasons, for example for a local detergent effect, or moisturizing, cosmetic, and/or even medicinal effects. In an alternative and simplified embodiment of the invention, the functions fulfilled by the liquid or gelatinous substances may also be obtained by selecting for construction of the head 3 a porous elastomeric material, that can be made to absorb, originally or at the time of use, said liquid or gelatinous substances, thereby being able to then release them directly in situ inside the ear canal. Functional intercommunication between the head 3 and the rod 2 may be obtained by capillary action.

Once said substances have produced the desired effect on the anatomical humours, in the heads 3 equipped with slits 8, said substances, moving through the slits 8 in the reverse direction, can collect inside the head 3 for subsequent conveying towards the outside of the stick 1, or be thrown away together with the stick in the form of waste.

In order to avoid any potential risk of physical separation of the head 3 from the rod 2, the connection of said component parts of the invention may be obtained by monolithic interconnection by means of sealing, gluing or sticking together the head 3 and the rod 2. In use, the stick 1 according to the invention allows hygienic treatment of the anatomical humours of the ear with: soft contact, of the elastically dampened type; in total safety for the user; with high operating effectiveness in terms of pick up and evacuation permitted by the grooved and toothed shape of the lateral surface of the head, as well as by the containment capacity of the head.

The invention adds to that the further advantage of the possibility of allowing accessory, preparatory or completion treatments, that are completely new compared with those allowed by the prior art.

Therefore, the invention fulfils the technical purpose that forms the basis of this invention, usefully and advantageously being able to be produced in disposable and re-usable formats.

The embodiment of the head 3 and of the rod 2 made of biodegradable material may also be further useful for minimising the environmental impact of sending the invention to landfill in the form of waste.

The invention described above is susceptible of evident industrial application. It may also be modified and adapted in several ways without thereby departing from the scope of the following claims.

Moreover, all details of the invention may be substituted by technically equivalent elements.

The invention claimed is:

1. A hygiene stick, for personal care, in particular for ear hygiene, comprising:
    a rod (2) for picking up and handling with fingers and having an axial line (5);
    at least one head (3) made of elastic material and having a tapered shape of geometric solid projecting from the rod along the axial line (5);
    at least one base interposed between and interconnected to said at least one head (3) and said rod (2), said at least one base is widened with respect to a line (10) transversal to the axial line (5), such that a width of said at least one head is equal to or less than a width of said at least one base;
    wherein the at least one head (3) is provided with a lateral surface (11) and wherein the at least one head defines a hollow inner space, and said lateral surface includes projections (12) extending upwardly between said at least one base and a top portion of said at least one head, wherein each of the projections has a helical shape wrapped around the axial line of the rod and wherein each pair of said projections define a channel therebetween such that said projections and said channels are alternately disposed with respect to a circular outline of the at least one head; and
    wherein each one of said channels includes a split which is in fluid communication with said hollow inner space.

2. The hygiene stick according to claim 1, wherein said at least one head (3) converges towards its free end (4) that is distal from the rod (2).

3. The hygiene stick according to claim 2, wherein said tapered shape is conical.

4. The hygiene stick according to claim 2, wherein said at least one head (3) is equipped with a rounded cap (6), supported at said free end (4).

5. The hygiene stick according to claim 1, wherein said at least one head (3) contains a liquid or gelatinous substance to be inserted in an ear canal through said slits (8).

6. The hygiene stick according to claim 1, wherein said rod (2) has a tubular shape communicating with said at least one head (3).

7. The hygiene stick according to claim 1, wherein said at least one head (3) is made of porous material, that can be made to absorb liquid or gelatinous substances.

8. The hygiene stick according to claim 1, wherein the stick is disposable.

9. The hygiene stick according to claim 8, wherein at least a material of said at least one head (3) is biodegradable.

10. The hygiene stick according to claim 1, wherein the stick is re-usable.

* * * * *